United States Patent [19]

Prutchi

[11] Patent Number: 5,578,064
[45] Date of Patent: Nov. 26, 1996

[54] RATE RESPONSIVE CARDIAC PACEMAKER WITH IMPEDANCE SENSING

[75] Inventor: David Prutchi, Lake Jackson, Tex.

[73] Assignee: Intermedics, Inc., Angleton, Tex.

[21] Appl. No.: 289,237

[22] Filed: Aug. 11, 1994

[51] Int. Cl.⁶ .................................................. A61N 1/368
[52] U.S. Cl. .............................. 607/19; 607/17; 128/734; 128/901
[58] Field of Search .................................. 607/18, 17, 20, 607/24; 128/670, 734, 671, 700, 901

[56] References Cited

U.S. PATENT DOCUMENTS

| | | |
|---|---|---|
| 4,686,987 | 8/1987 | Salo et al. ........................ 128/419 PG |
| 4,688,573 | 8/1987 | Alt . |
| 4,702,253 | 10/1987 | Nappholz et al. . |
| 4,901,725 | 2/1990 | Nappholz et al. ................. 128/419 PG |
| 5,154,171 | 10/1992 | Chirife et al. .................... 128/419 PG |
| 5,197,467 | 3/1993 | Steinhaus et al. ................. 128/419 PG |
| 5,201,808 | 4/1993 | Steinhaus et al. ................. 128/419 PG |
| 5,271,395 | 12/1993 | Wahlstrand et al. ....................... 607/9 |
| 5,441,524 | 8/1995 | Rueter et al. ............................. 607/18 |

Primary Examiner—Marvin M. Lateef
Assistant Examiner—Kennedy J. Schaetzle
Attorney, Agent, or Firm—John R. Merkling

[57] ABSTRACT

An implantable, rate responsive pacemaker, sensitive to impedance changes in the heart as an indicator of cardiac stroke volume, wherein the baseline impedance is eliminated from the measurement of impedance. In one embodiment, an adaptively controlled, balanced bridge is utilized to eliminate the baseline. A Wein bridge is provided having a variable reactance whose impedance is controlled continuously. In another embodiment, an impedance measurement is modified by a signal conditioner providing an appropriate varying offset through the use of a sample and hold circuit and other signal modifying circuits prior to converting the impedance measurement to digital information. In a third embodiment, a sample and hold circuit may be used to provide digital information through an A to D converter to a microprocessor which directly controls a variable reactance. The end voltage of a pacing capacitor is used as an indication of a baseline impedance.

46 Claims, 4 Drawing Sheets

RATE RESPONSIVE CARDIAC PACEMAKER WITH IMPEDANCE SENSING

FIELD OF MY INVENTION

My invention relates to rate responsive cardiac pacemakers, and more particularly to cardiac pacemakers which automatically adjust their pacing rate in response to measured impedance, and most particularly in response to measured impedance changes in the heart.

BACKGROUND OF MY INVENTION

Implanted cardiac pacemakers are employed to assist patients suffering from severe bradycardia or chronotropic incompetence. Originally, such pacemakers restored a normal, at rest, heart rate by providing a fixed rate or narrow range of externally programmable rates. However, these pacemakers failed to meet patients' metabolic demands during exercise. Consequently, so-called "rate adaptive" or "rate responsive" pacemakers were developed. These pacemakers sense some parameter correlated to physiologic need and adjust the pacing rate of the pacemaker.

Numerous parameters have been selected to attempt to correlate pacing rate to the actual physiologic need of the patient. Blood pH, blood temperature, QT interval, vibration, respiration rate, or accelerations due to physical activity have been employed with varying degrees of success. Among these parameters are the stroke volume of the heart and the minute volume of respiration, both parameters being inferred from impedance measurements. The stroke volume of the heart is defined as the volume of blood expelled by the ventricle in a single beat. It is equal to the difference between the end diastolic volume and the end systolic volume. In normal human subjects with healthy hearts, the stroke volume of the heart has been found to remain relatively constant over a wide range of exertion. Increases in cardiac output required to meet physiologic needs are primarily provided by increased heart rate. For certain patients with pacemakers whose heart rate is controlled by the pacemaker, increased cardiac output during exertion is provided by the heart attempting to increase its stroke volume. The stroke volume cannot increase, however, by a factor more than about two to two and a half times. Increasing the pacing rate is therefore still desired. It has been proposed to utilize the body's tendency to attempt to increase stroke volume to adjust the pacing rate of an implanted pacemaker, thereby providing an appropriate physiologic pacing rate.

For example, in Salo et al., U.S. Pat. No. 4,686,987 a stroke volume responsive, rate adjusting pacemaker is described. An AC signal is inserted through an implanted lead. The changing volume of the heart alters the impedance between the lead electrode and another electrode or the can of the pacemaker, and the changing impedance modulates the detected AC signal. By isolating the resulting amplitude envelope, an indication of the changing impedance can be obtained. This fluctuation is deemed to be a function, at least in part, of the action of the heart.

Chirife, U.S. Pat. No. 5,154,171, proposed that metabolic demands should be related to the ejection fraction, as a more accurate measure of true physiologic need. The ejection fraction is the stroke volume divided by the end diastolic volume. The stroke volume is taken to be the end diastolic volume minus the end systolic volume. The observed impedance of the heart is deemed to be a function of volume of the heart and therefore to be an indication of the desired measurements when taken at an appropriate time.

The impedance of the body, however, is not solely related to the beating of the heart. Other motions and factors also change the impedance characteristics. One example is change due to respiration. It has been proposed that the minute volume of respiration could be detected by an appropriate impedance measurement. See, for example, U.S. Pat. No. 4,901,725 entitled "Minute Volume Rate Responsive Pacemaker" to Nappholz et al.

U.S. Pat. No. 5,201,808 to Steinhaus et al., describes several attempts to detect the minute volume due to respiration in an accurate manner. Steinhaus et al. also proposes a relatively high frequency wave form as the appropriate means for measuring the spatial impedance as a function of the patient's pleural pressure. Steinhaus et al. notes that different frequencies for the testing pulse are adapted to detecting different phenomenon. That is, one range of frequency may be more appropriate for detecting changes due to heart beats, another would be more appropriate for detecting minute volume.

Another problem raised by the use of impedance as an indirect measure of physiologic need is the indeterminate current path. The impedance of the body is generally measured between at least two points within the body, perhaps an electrode in the heart and a second electrode or the can of an implanted device. The path between these to points, however, is inherently indeterminate. Moreover, it may be affected by motion of the electrode tip, by conditions surrounding the tip or by electrical capacitances adjacent the electrode (as described in Steinhaus et al. '808), or other factors. In general, however, these factors are relatively slow to change, as compared to changes in impedance due to the beating of the heart. Moreover, I have observed that changes in impedance due to heart beats are usually on the order of 0.5 to 10 ohms whereas long-term changes, representing a baseline impedance, have a magnitude of about 500 ohms and tend to vary over a range of several hundred ohms. It is desirable, therefore, to eliminate or minimize the effect of background or baseline impedance so that changes in impedance due to the relatively fast beating heart may be amplified and more easily detected.

SUMMARY OF MY INVENTION

I have invented an implantable, rate responsive pacemaker, sensitive to impedance changes in the heart as an indicator of cardiac stroke volume, wherein the baseline impedance is eliminated from the measurement of impedance. This enhances the pacemaker ability to distinguish cardiac-related changes in impedance.

In one embodiment of my invention, an adaptively controlled, balanced bridge is utilized to eliminate the typical 500 ohm wandering, low-frequency baseline and thereby enhance the varying impedance signal components related to cardiac function. A Wein bridge is provided having a variable reactance whose impedance is controlled continuously but at a relatively slow rate, to attempt to balance the Wein bridge output to zero. Because changes in impedance due to cardiac action are relatively high frequency, they are not followed by the feedback mechanism and can be measured for cardiac pacer rate control.

In another embodiment of my invention, an impedance measurement can be modified by a signal conditioner providing an appropriate varying offset through the use of a sample and hold circuit and other signal modifying circuits prior to converting the impedance measurement to digital information.

In a third embodiment of my invention, a sample and hold circuit may be used to provide digital information through an A-to-D converter to a microprocessor which directly controls a variable reactance. Such a circuit might sample the end voltage of a pacing capacitor as an indication of a baseline impedance.

It is the principal object of my invention, therefore, to provide a rate-responsive pacemaker which can more accurately detect impedance changes in the heart.

A further object of my invention is to provide an impedance sensitive pacemaker which can reject baseline or background impedance.

Another object of my invention is to provide a rate responsive pacemaker which can amplify the effects of cardiac related impedance changes.

Another important object of my invention is to provide a rate responsive pacer which is more selectively responsive to cardiac stoke volume changes, as indicated by changes in cardiac impedance.

These and other objects and features of my invention will be apparent to the skilled artistan from the following detailed description taken with reference to the accompanying drawings.

DETAILED DESCRIPTION OF MY PREFERRED EMBODIMENT

I will now describe the preferred embodiments of my invention with reference to the accompanying figures. Like numerals will be used to designate like parts throughout.

Figure 1:
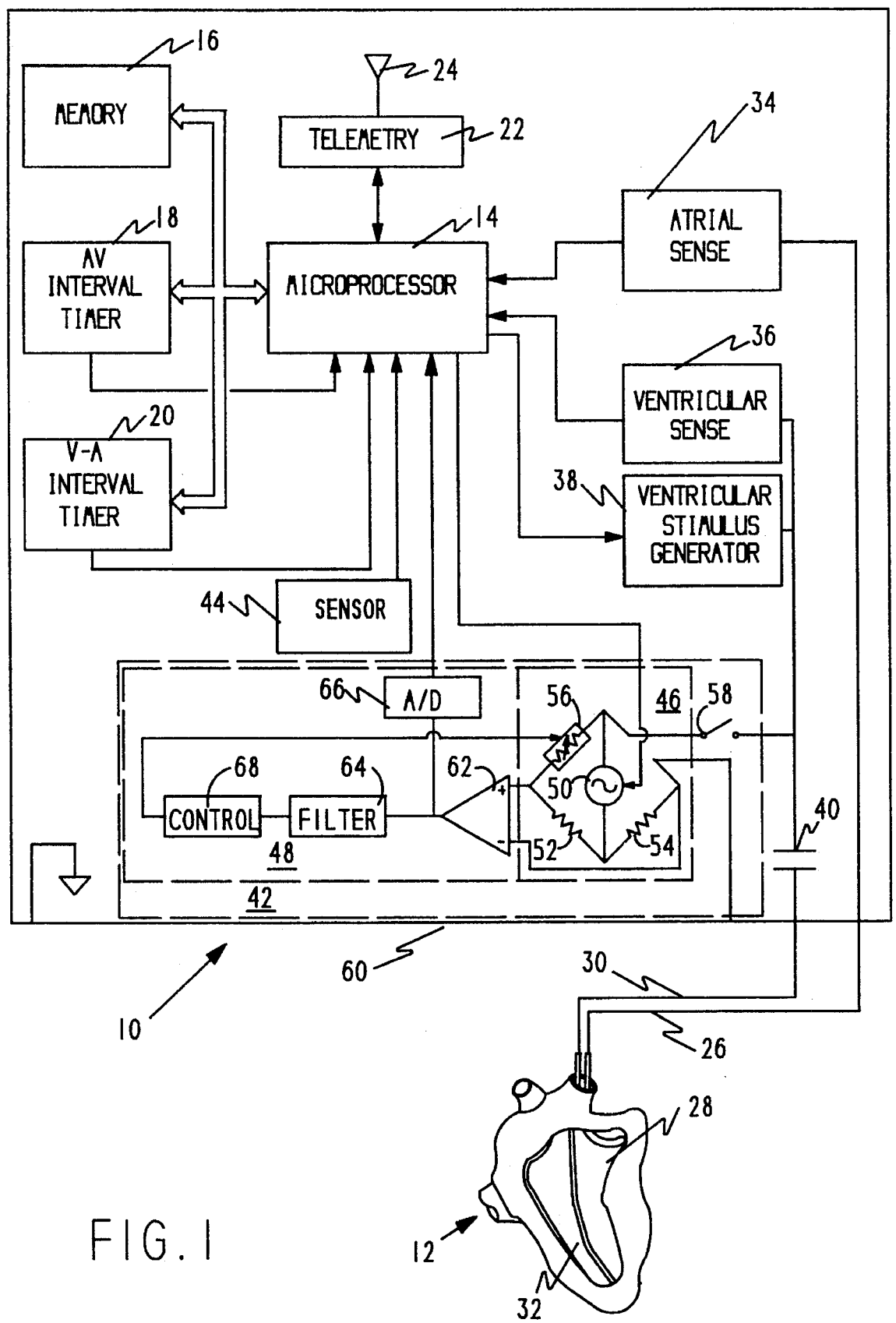
FIG. 1 is a block diagram of a first preferred embodiment of a rate adaptive pacemaker according to my invention.

Referring now to FIG. 1, a pacemaker, generally designated 10, is illustrated in schematic fashion with connection to a human heart 12. For ease of illustration, I have elected to describe my invention in connection with a pacemaker having atrial sensing and ventricular sensing and pacing. It should be understood, however, that my invention can be employed for sensing in the atrium, the ventricle or both and that both atrial or ventricular pacing could be provided without departing from the teachings of my invention. In addition, the features of my invention could also be combined with an implantable defibrillator/cardiovertor.

With this understanding, the illustrated pacemaker 10 comprises a microprocessor 14 which executes various control programs to regulate the action of the pacemaker. The microprocessor 14 is connected to additional memory 16 for the storage of programs and data as may be needed. As is known in the art, one or more internal clocks may be provided to permit timing of various events. For example, an A-V interval timer 18 may be provided. Similarly, a V-A interval timer 20 may also be provided, as known in the art. The microprocessor is provided with a telemetry circuit 22 so that communication can be had across an antenna 24 to an external programmer (not shown). Telemetry permits an attending physician to obtain data and information from the pacemaker and to control the pacemaker to set various selectable parameters, as known in the art.

The pacemaker 10 is connected to the heart 12 through a first lead 26 to the atrium 28 and through a second lead 30 to the ventricle 32. In the illustrated embodiment, atrial sensing, through an atrial sense circuit 34, and ventricular sensing, through a ventricular sense circuit 36, provide information to the microprocessor concerning the condition and responsiveness of the heart. In addition, pacing pulses are provided to the ventricle from a ventricular stimulus generator 38. It is clearly within the scope of those skilled in the art to provide atrial pacing, should that be desired, or to provide cardioversion/defibrillation capabilities in response to the detected condition of the heart. Stimulation of the heart is passed through a coupling capacitor 40 in a conventional fashion.

To control the pulse rate of the ventricular stimulus generator 38, the microprocessor acquires information on the condition of the heart through an impedance circuit 42. The impedance circuit 42 detects changes in impedance primarily due to the changing shape of the heart, which is related to the physical shape of the heart as it beats and pumps blood. This information can be used to derive a measure of the stroke volume or ejection fraction of the heart.

In addition to the measurement of impedance, a sensor 44 may also be provided to obtain an indication of physiologic need and adjust the pacing rate. Such a sensor may be an accelerometer, as described by Dahl, U.S. Pat. No. 4,140,132 a temperature sensor, as described by Alt, U.S. Pat. No. 4,688,573, or any other suitable sensor of a parameter which may be correlated to physiologic need of the patient.

The impedance circuit 42 comprises an adaptively controlled Wein bridge 46 connected to the ventricular lead 30, and signal processing circuitry 48. The Wein bridge 46 comprises a signal generator 50 which is controlled by the microprocessor. It is preferred that the signal generator produce an AC carrier signal or one or more narrow pulses or a similar signal. A suitable AC carrier would have a frequency in the range of about 100 Hz to 500 kHz, preferably about 10 kHz. Pulses should have a duration of from about 0.1 μsec to 1 msec, although other durations could be chosen. Two balanced reactances 52, 54 form two of the legs of the bridge 46. A third leg is formed by a variable reactance 56 which is controlled by the signal processing circuitry 48. The fourth leg of the Wein bridge is connected through the heart by way of a switch 58, the lead 30, a path through the heart and some of the body tissue to the pacemaker can 60. Of course, a bipolar lead could also be utilized instead of the unipolar lead illustrated. The switch 58 is controlled by the microprocessor so that sensing of impedance is interrupted at appropriate times, as when the heart is being paced.

The Wein bridge 46 is connected to a differential amplifier 62 in the signal processing circuitry 48. The output of the differential amplifier is passed both to a band pass filter 64 and to a signal converter 66. The signal converter 66 may be an A-to-D converter or a delta modulator or a similar circuit. The band pass filter 64 rejects the relatively high frequency changes resulting from the contractions of the heart while passing the larger, lower frequency components associated with a baseline impedance to a control circuit 68 which adjusts the variable reactance 56. The variable reactance 56 may be implemented using a switched capacitor circuit or an operational transconductance amplifier, or other variable reactance which can be controlled appropriately in the low-power environment of the pacemaker 10.

Figure 4:
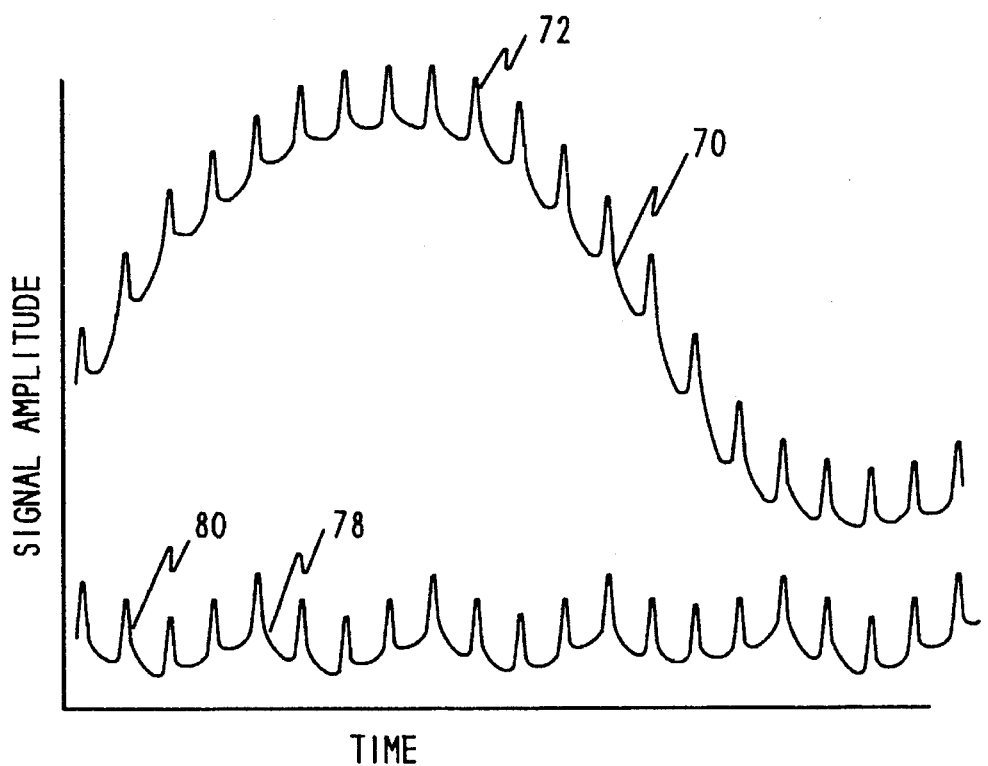
FIG. 4 is a graph of signal amplitude versus time of measured cardiac signals.
Figure 5:
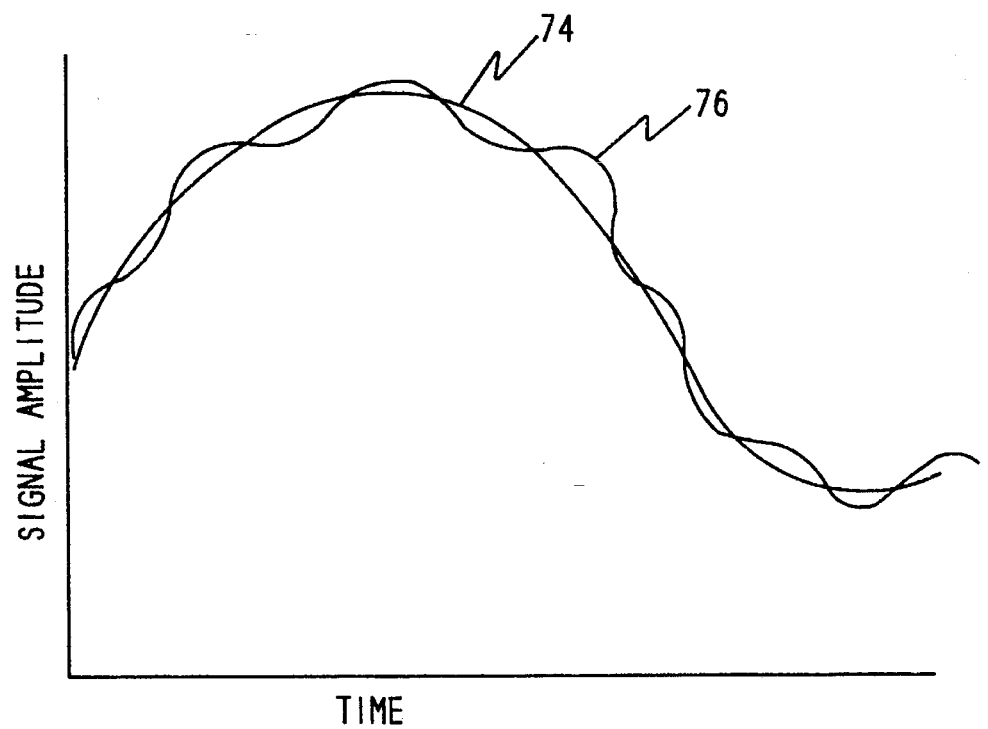
FIG. 5 is a graph of signal amplitude versus time of an impedance baseline and feedback control signal.

The effect of the impedance circuit 42 can best be understood in connection with FIGS. 4 and 5. In FIG. 4, a first variable signal 70 is illustrated as the upper signal in FIG. 4. This signal represents the measured voltage through the signal converter 66 resulting from insertion of a test signal from the signal generator 50, without the effect of the adaptive reactance of the impedance circuit 42. There are small recurrent features such as feature 72 which are associated with the contraction of the heart. The overall shape of the curve 70 is dictated more by a baseline or background impedance, which may be the result of respiration, physical condition of the body, orientation of the body or other factors. This baseline, extracted from the signal 70, is shown in FIG. 5 as line 74.

To eliminate the effects of the baseline, the band pass filter 64 and the control circuit 68 produce a control signal represented by the graph line 76 in FIG. 5, which closely tracks the actual baseline 74. By inserting this signal to control the variable reactance 56, the output of the differential amplifier 62 is modified from that of signal 70 to signal 78 in FIG. 4. Clearly the major feature in signal 78 is the effects due to the cardiac contractions, such as the effect at numeral 80, rather than the baseline impedance changes. This signal, therefore, can be amplified or analyzed to a finer degree by the microprocessor and more accurate response to cardiac-related changes can therefore be expected.

Figure 2:
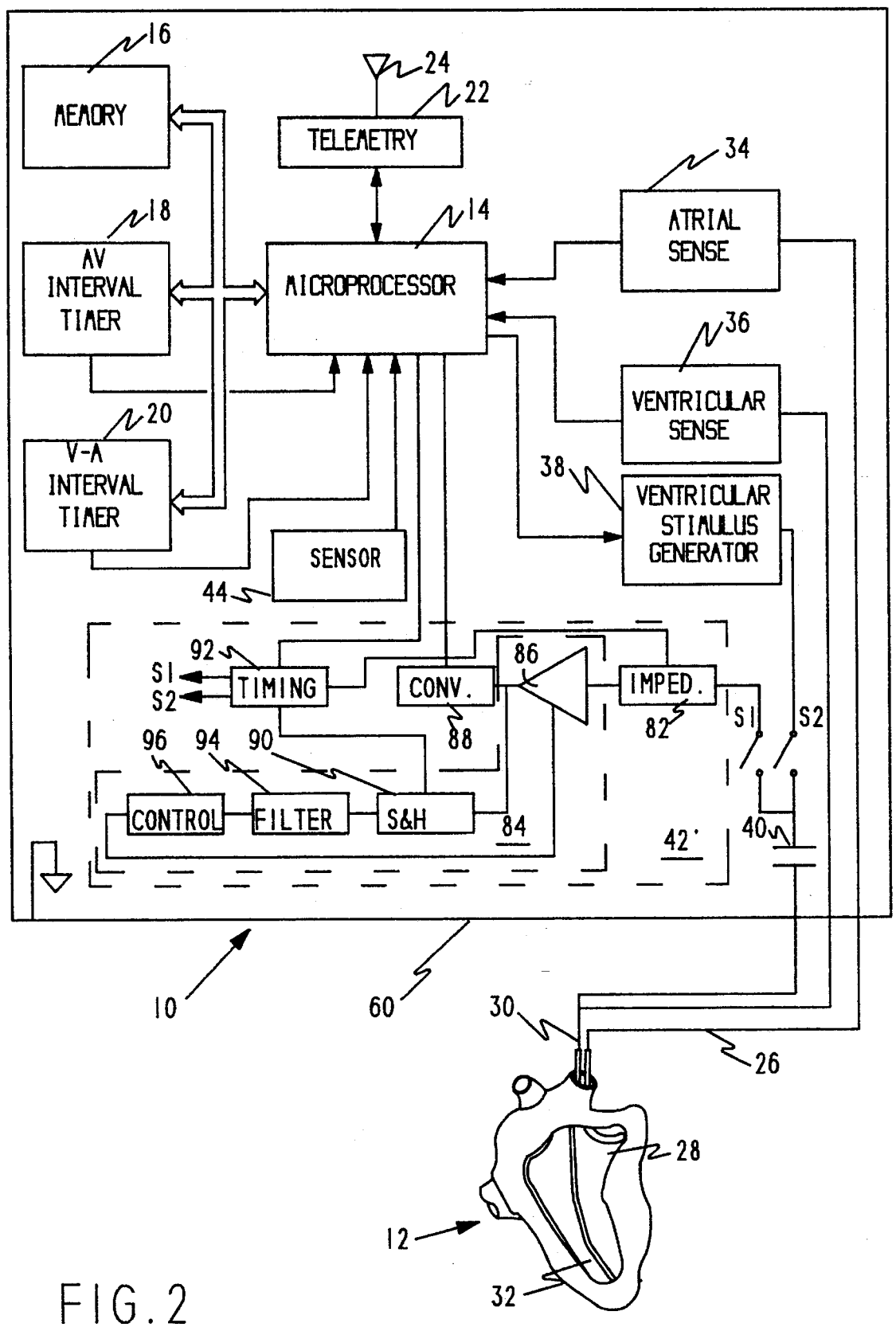
FIG. 2 is a block diagram of second embodiment of a rate adaptive pacemaker according to my invention.

A second embodiment of my invention is illustrated in FIG. 2. Features already described in connection with FIG. 1 are labeled with similar numbers, and a description will not be repeated here. In this instance, the impedance circuit, here labeled 42', utilizes a control circuit to adaptively provide an offset control to the operational amplifier.

An impedance signal and raw impedance measurement are obtained through an impedance measurement circuit 82. This impedance measurement circuit 82 produces a test signal, as in the embodiment of FIG. 1, and detects variation in the signal as a measure of the impedance. The resulting impedance signal is communicated to a signal conditioner 84 which comprises an offset-controlled operational amplifier 86. The output of the operational amplifier 86 passes to a signal converter 88, similar to the signal converter 66 described above in connection with FIG. 1, which communicates the signal to the microprocessor 14. The output of the operational amplifier 86 is then transferred to a control circuit 90. Sampling through the control circuit 90 of the output of the operational amplifier 86 is controlled by a timing circuit 92 under the direction of the microprocessor 14. The timing circuit 92 also controls two switches S1 and S2 which selectively connect the ventricular stimulus generator and the impedance circuit 42' to the lead 30. The value sampled by the control circuit 90 is conditioned by a band pass filter 94 to reject higher frequency components associated with cardiac contractions while passing lower frequency components associated with a variable baseline. A control circuit 96 produces an appropriate signal to provide an offset to the operational amplifier, adaptively eliminating the baseline from the output of the operational amplifier.

Figure 3:
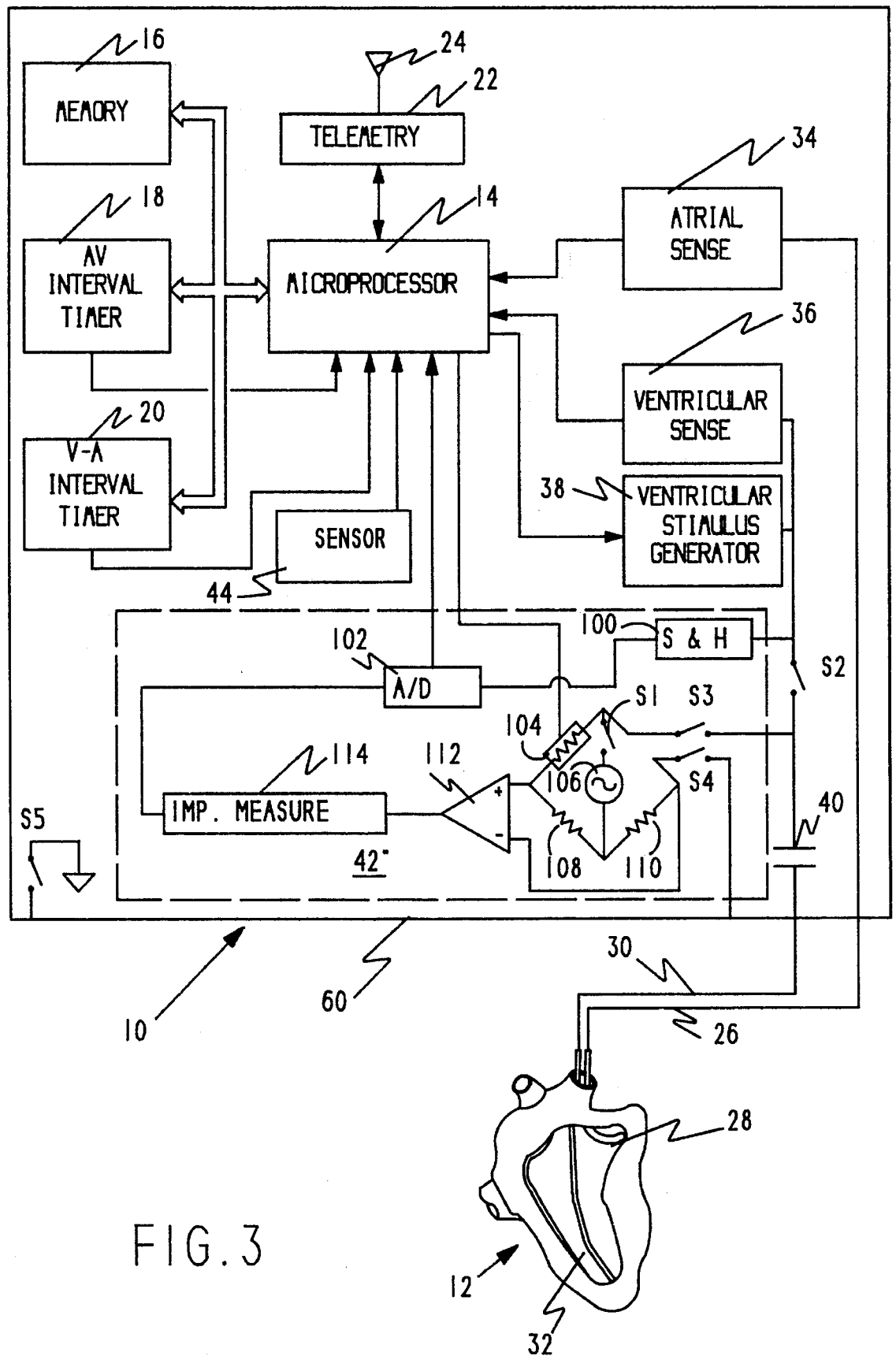
FIG. 3 is a block diagram of third embodiment of a rate adaptive pacemaker according to my invention.

A third embodiment of my invention is illustrated in FIG. 3. Again, elements of the pacer 10 which were common to the embodiments of FIG. 1 and FIG. 2 are labeled with similar numbers and are not described again here. In this case an impedance measurement circuit 42" utilizes the voltage remaining on a pacing capacitor after a pace as an indication of the baseline impedance. The pacing capacitor is a known part of a stimulus generator 38. This provides an offset to eliminate the baseline impedance from a general impedance measurement. The microprocessor 14 controls switches S1, S2, S3 and S4 to connect the components of the circuit at appropriate times during the cardiac cycle. For example, switches S3 and S4 must be disconnected when S2 is closed both for pacing and to sample the end voltage on the pacing capacitor. During pacing, S3 and S4 are open and S2 and S5 (connecting the can to ground) are closed for the selected pacing pulse duration. A pacing capacitor in the ventricular stimulus generator discharges through the coupling capacitor 40 to stimulate the heart. At the end of the pulse, S2 or S5 or both are opened. The remaining voltage on the pacing capacitor in the stimulus generator 38 can be measured by the microprocessor 14 through a sample-and-hold circuit 100 and A-to-D convertor 102. Since the pulse length (duration) is known and the initial voltage on the pacing capacitor and its capacitance are also known, the impedance of the output circuit and the lead can be calculated by the microprocessor. Using a series of values, the trend of the impedance baseline can be computed by the microprocessor, for example, by using a running average. This average impedance value may be assigned from time to time by the microprocessor to a controllable reactance 104. When pacing is not occurring and the switches S2 and S5 are opened, switches S3 and S4 are closed so that the varying components of the impedance associated with cardiac contractions can be measured. The microprocessor controls a signal generator 106 in the Wein bridge which includes reactances 108, 110. The output of the Wein bridge is coupled to a differential amplifier 112. The output of the differential amplifier 112 can be processed through an impedance measurement circuit 114 which may comprise a sample-and-hold circuit and appropriate band pass filters. Thereafter the signal is communicated to the microprocessor 14 through the A-to-D converter 102.

Having identified impedance information associated with cardiac contractions, this information can then be used to control the pacing rate. By controlling the pacing rate in such a manner as to keep the stroke volume relatively constant from cycle to cycle, a physiologically appropriate pacing rate is selected.

My invention may be embodied in other specific forms without departing from the spirit or essential characteristics thereof. The foregoing description is, therefore, to be viewed in all respects as illustrative and not restrictive. The scope of my invention is defined by the appended claims.

I claim as my invention:

1. A rate responsive cardiac pacemaker comprising pulse generator means for stimulating the heart of a patient to contract;

means for controlling the rate of pulse generation by said pulse generator means;

means for producing an electrical signal proportional to a changing impedance within the body of the patient, at least part of said changing impedance being caused by action of the heart;

means for adaptively selecting a portion of said signal, said adaptively selected portion being related to non-cardiac factors in the body of the patient;

means for attenuating said adaptively selected portion to produce an adaptively filtered signal;

means for amplifying said adaptively filtered signal to produce an amplified adaptively filtered signal; and means for adjusting said rate controlling means as a function of said amplified adaptively filtered signal.

2. The cardiac pacemaker according to claim 1 further comprising sensor means for detecting a non-impedance parameter correlated to physiologic need of said patient and means for adjusting said rate controlling means as a function of said detected parameter.

3. The cardiac pacemaker according to claim 2 wherein said sensor means is an accelerometer.

4. The cardiac pacemaker according to claim 2 wherein said sensor means is a temperature sensor.

5. The cardiac pacemaker according to claim 1 wherein said means for adaptively selecting a portion of said signal comprise a Wein bridge.

6. The cardiac pacemaker according to claim 5 wherein said Wein bridge comprises a variable reactance.

7. The cardiac pacemaker according to claim 6 further comprising sensor means for detecting a non-impedance parameter correlated to physiologic need of said patient and means for adjusting said rate controlling means as a function of said detected parameter.

8. The cardiac pacemaker according to claim 7 wherein said sensor means is an accelerometer.

9. The cardiac pacemaker according to claim 7 wherein said sensor means is a temperature sensor.

10. The cardiac pacemaker according to claim 6 wherein said variable reactance comprises a switched capacitor circuit.

11. The cardiac pacemaker according to claim 6 wherein said variable reactance comprises an operational transconductance amplifier.

12. The cardiac pacemaker according to claim 6 wherein said means for adaptively selecting a portion of said signal further comprise a differential amplifier connected in a feed back loop to said variable reactance.

13. The cardiac pacemaker according to claim 12 wherein said means for adjusting said rate controlling means comprise a microprocessor electrically connected to said differential amplifier.

14. The cardiac pacemaker according to claim 13 wherein said feed back loop comprises a band-pass filter circuit.

15. The cardiac pacemaker according to claim 14 further comprising sensor means for detecting a non-impedance parameter correlated to physiologic need of said patient and means for adjusting said rate controlling means as a function of said detected parameter.

16. The cardiac pacemaker according to claim 15 wherein said sensor means is an accelerometer.

17. The cardiac pacemaker according to claim 15 wherein said sensor means is a temperature sensor.

18. The cardiac pacemaker according to claim 1 wherein said means for adaptively selecting a portion of said signal comprise means for adjusting an impedance signal to off set said baseline impedance.

19. The cardiac pacemaker according to claim 18 wherein said means for adjusting said impedance signal comprise an off-set controlled operational amplifier and a feed-back loop for controlling said off-set.

20. The cardiac pacemaker according to claim 19 wherein said means for adjusting said rate controlling means comprise a microprocessor electrically connected to said operational amplifier.

21. The cardiac pacemaker according to claim 20 further comprising sensor means for detecting a non-impedance parameter correlated to physiologic need of said patient and means for adjusting said rate controlling means as a function of said detected parameter.

22. The cardiac pacemaker according to claim 21 wherein said sensor means is an accelerometer.

23. The cardiac pacemaker according to claim 21 wherein said sensor means is a temperature sensor.

24. The cardiac pacemaker according to claim 20 wherein said feed-back loop further comprises a sample and hold circuit.

25. The cardiac pacemaker according to claim 20 wherein said feed-back loop further comprises a band-pass filter.

26. The cardiac pacemaker according to claim 25 wherein said feed-back loop further comprises a sample and hold circuit.

27. The cardiac pacemaker according to claim 1 wherein said means for adaptively selecting a portion of said signal comprises means electrically connected to said pulse generator means for detecting charge remaining in said pulse generator means after a pulse.

28. The cardiac pacemaker according to claim 27 wherein said means for detecting charge comprise a sample and hold circuit.

29. The cardiac pacemaker according to claim 27 wherein said means for adjusting said rate controlling means comprise a Wein bridge having a variable reactance and means for controlling said variable reactance as a function of said detected remaining charge.

30. The cardiac pacemaker according to claim 29 wherein said means for adjusting said rate controlling means further comprise a differential amplifier connected to said Wein bridge for providing said amplified adaptively filtered signal.

31. The cardiac pacemaker according to claim 30 further comprising sensor means for detecting a non-impedance parameter correlated to physiologic need of said patient and means for adjusting said rate controlling means as a function of said detected parameter.

32. The cardiac pacemaker according to claim 31 wherein said sensor means is an accelerometer.

33. The cardiac pacemaker according to claim 31 wherein said sensor means is a temperature sensor.

34. The cardiac pacemaker according to claim 30 wherein said means for adjusting said rate controlling means further comprise a microprocessor for receiving said signal from said differential amplifier and providing a control signal to said pulse generator means.

35. The cardiac pacemaker according to claim 34 wherein said means for adjusting said rate controlling means further comprises impedance measurement means for processing said signal from said differential amplifier and for communicating a processed signal to said microprocessor.

36. The cardiac pacemaker according to claim 35 wherein said impedance measurement means comprise a sample and hold circuit.

37. The cardiac pacemaker according to claim 35 wherein said impedance measurement means comprise a band-pass filter.

38. The cardiac pacemaker according to claim 37 wherein said impedance measurement means comprise a sample and hold circuit.

39. A rate responsive cardiac pacemaker comprising pulse generator means for stimulating the heart of a patient to contract;

means for controlling the rate of pulse generation by said pulse generator means;

means for detecting a changing impedance within the body of the patient, at least part of said changing impedance being caused by action of the heart;

means for isolating a baseline impedance from said changing impedance, said baseline impedance being related to non-cardiac factors in the body of the patient, said means for isolating said baseline impedance comprising an off-set controlled operational amplifier and a feed-back loop for controlling an off-set of said operational amplifier;

means for adjusting said rate controlling means as a function of the difference of said changing impedance and said baseline impedance.

40. The cardiac pacemaker according to claim 39 wherein said means for adjusting said rate controlling means comprise a microprocessor electrically connected to said operational amplifier.

41. The cardiac pacemaker according to claim 40 further comprising sensor means for detecting a non-impedance parameter correlated to physiologic need of said patient and means for adjusting said rate controlling means as a function of said detected parameter.

42. The cardiac pacemaker according to claim 41 wherein said sensor means is an accelerometer.

43. The cardiac pacemaker according to claim 41 wherein said sensor means is a temperature sensor.

44. The cardiac pacemaker according to claim 40 wherein said feed-back loop further comprises a sample and hold circuit.

45. The cardiac pacemaker according to claim 40 wherein said feed-back loop further comprises a band-pass filter.

46. The cardiac pacemaker according to claim 45 wherein said feed-back loop further comprises a sample and hold circuit.

* * * * *